(12) United States Patent
Yuan et al.

(10) Patent No.: US 12,071,388 B2
(45) Date of Patent: Aug. 27, 2024

(54) FULL CONTINUOUS FLOW SYNTHESIS PROCESS OF FLUORINE-CONTAINING AROMATIC HYDROCARBON COMPOUNDS

(71) Applicants: Fujian Zhongxin Fluoride Material Gaobao Technology Co., Ltd., Sanming (CN); Zhejiang Zhongxin Fluoride Materials Co., Ltd., Shaoxing (CN)

(72) Inventors: Qiliang Yuan, Shaoxing (CN); Yongyi Miao, Shaoxing (CN); Yonggen Shi, Shaoxing (CN); Yiqiang Zhang, Shaoxing (CN); Yinhao Chen, Shaoxing (CN); Chao Wang, Shaoxing (CN)

(73) Assignees: Fujian Zhongxin Fluoride Material Gaobao Technology Co., Ltd., Sanming (CN); Zhejiang Zhongxin Fluoride Materials Co., Ltd., Shaoxing (CN)

(*) Notice: Subject to any disclaimer, the term of this patent is extended or adjusted under 35 U.S.C. 154(b) by 383 days.

(21) Appl. No.: 17/544,895

(22) Filed: Dec. 7, 2021

(65) Prior Publication Data
US 2022/0204427 A1   Jun. 30, 2022

Related U.S. Application Data

(63) Continuation of application No. PCT/CN2021/099262, filed on Jun. 10, 2021.

(30) Foreign Application Priority Data

Dec. 24, 2020  (CN) .......................... 202011550607.9

(51) Int. Cl.
C07C 17/07      (2006.01)
B01J 19/00      (2006.01)

(52) U.S. Cl.
CPC ........... *C07C 17/07* (2013.01); *B01J 19/0013* (2013.01); *B01J 19/0093* (2013.01); *B01J 2219/00905* (2013.01)

(58) Field of Classification Search
CPC ....... C07C 17/07; C07C 17/38; C07C 17/383; C07C 17/093; C07C 25/13; B01J 19/0013; B01J 19/0093; B01J 2219/00905
See application file for complete search history.

(56) References Cited

FOREIGN PATENT DOCUMENTS

| CN | 110283039 A | 9/2019 |
|---|---|---|
| CN | 111116303 A | 5/2020 |

(Continued)

OTHER PUBLICATIONS

Internation Search Report of PCT/CN2021/099262, Mailed Sep. 8, 2021.

*Primary Examiner* — Jafar F Parsa

(57) ABSTRACT

A full continuous flow synthesis process of fluorine-containing aromatic hydrocarbon compounds. Aromatic amine and hydrogen fluoride are respectively pumped into thermostats A and B, then flow into micro-channel reactor C for salt forming reaction whose temperature is kept constant; sulfuric acid solution of nitrosylsulfuric acid is pumped into thermostat D; after keeping the temperature constant, the sulfuric acid solution of nitrosylsulfuric acid and salt forming product flowing out from the micro-channel reactor C flow into micro-channel reactor E for diazotization reaction; the obtained product flows into micro-channel reactor F for thermal decomposition reaction, is cooled in cooler G, then enters three-phase separator H for continuous separation, fluorine-containing aromatic hydrocarbon crude product is subjected to continuous alkaline washing, drying and rectification to obtain fluorine-containing aromatic hydrocarbon finished product, and mixture of hydrofluoric acid and (Continued)

sulfuric acid is continuously distilled to obtain hydrogen fluoride and sulfuric acid.

23 Claims, 1 Drawing Sheet

(56) References Cited

FOREIGN PATENT DOCUMENTS

| | | |
|---|---|---|
| CN | 112608212 A | 4/2021 |
| EP | 0357671 A1 | 3/1990 |

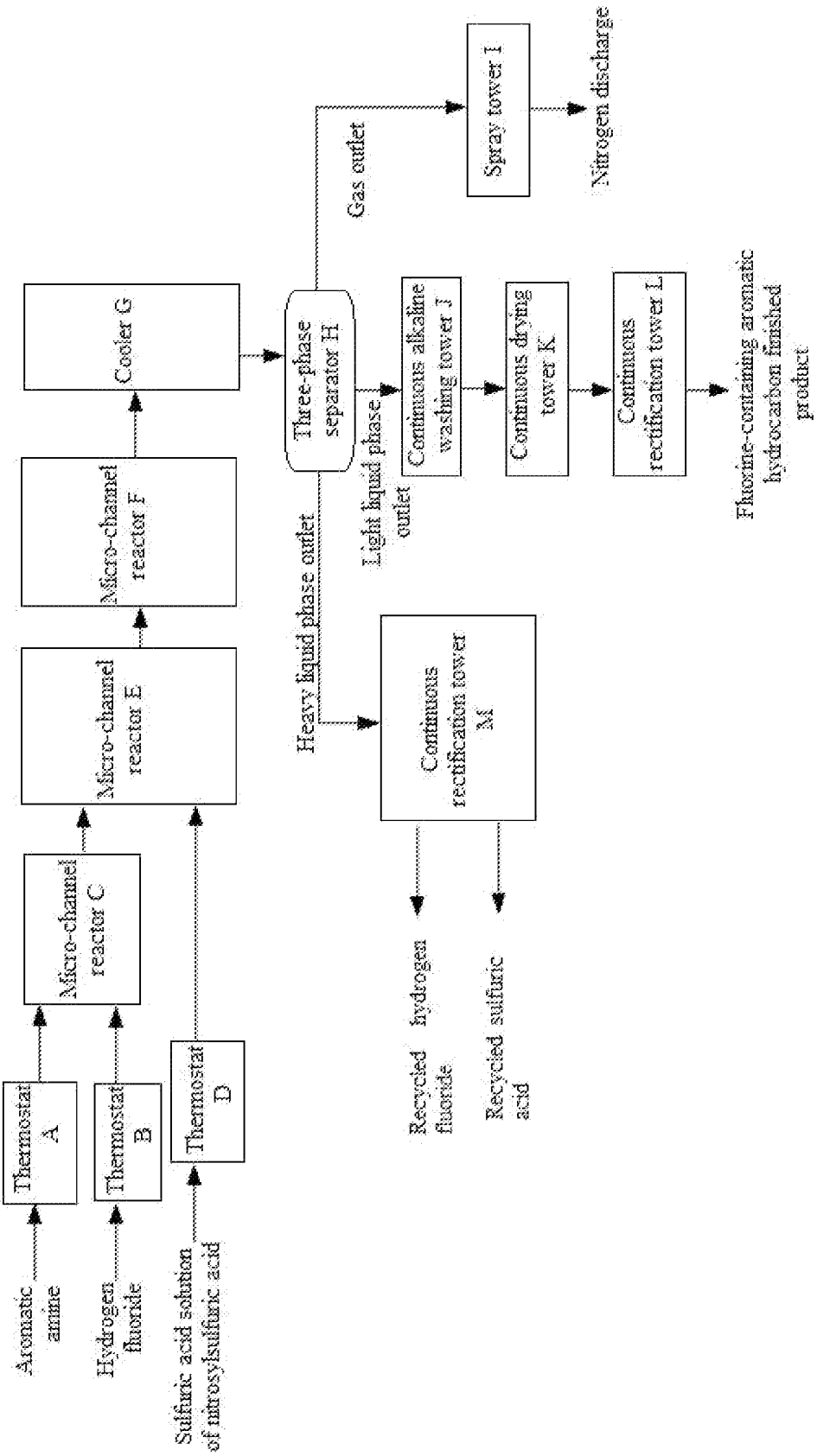

FULL CONTINUOUS FLOW SYNTHESIS PROCESS OF FLUORINE-CONTAINING AROMATIC HYDROCARBON COMPOUNDS

CROSS-REFERENCE TO RELATED APPLICATIONS

This application is a continuation of International Patent Application No. PCT/CN2021/099262 with a filing date of Jun. 10, 2021, designating the United States, now pending, and further claims priority to Chinese Patent Application No. 202011550607.9 with a filing date of Dec. 24, 2020. The content of the aforementioned applications, including any intervening amendments thereto, are incorporated herein by reference.

TECHNICAL FIELD

The disclosure relates to a full continuous flow synthesis process of fluorine-containing aromatic hydrocarbon compounds, belonging to the technical field of halohydrocarbon carbocycle organic compounds.

BACKGROUND OF THE PRESENT INVENTION

Fluorine-containing aromatic hydrocarbon compounds, such as fluorobenzene and methyl fluorobenzene, are important basic raw materials of aromatic fluorides. They not only can be directly used for synthesis of medicines, pesticides and dyes, but also can be used for synthesizing a variety of fluorobenzene derivatives through nitration, chlorination and acylation reactions to be applied in the above fields. In recent years, the fluorine-containing aromatic hydrocarbon compounds can also be used for the fields of special engineering plastic preparation and the like, and have extremely wide use and market demands increased year by year. The industrial production methods of the fluorine-containing aromatic hydrocarbon compounds mainly include: a Baz schimann method, a halogen exchange method and a hydrogen fluoride method. The Baz schimann method is a common method in production of fluorine-containing aromatic hydrocarbon compounds, but it needs to consume lots of tetrafluoroboric acid; in the process of thermal decomposition, nitrogen is generated and meanwhile a strong-corrosive and toxic boron trifuloride gas is released, leading to a fact that the environment is seriously polluted; and production process has a large potential safety hazard, thus the Baz schimann method is gradually facing the pressure of elimination. Relative to the Baz schimann method, the halogen exchange method is simple in production operation and low in safety risk, but is only suitable for halogenated aromatic hydrocarbons with strong electron absorbing groups on a benzene ring, so it has a narrow application range. The hydrogen fluoride method is improvement of the Baz schimann method and avoids the use of tetrafluoroboric acid, thus the strong-corrosive and toxic boron trifluoride gas is not generated in the process of thermal decomposition, and the safety of reaction and friendliness of environment are promoted to a certain extent. However, the hydrogen fluoride method has the disadvantages that a large amount of hydrogen fluoride is used in the process of reaction, and the production process still has large potential safety hazard due to a low boiling point, high volatility, high corrosivity and high toxicity of hydrogen fluoride. Therefore, how to reduce the holdup and fugitive volatilization of hydrogen fluoride in the process of production and promote the safety of the production process directly determines the application range of the hydrogen fluoride method.

At present, the hydrogen fluoride method has been applied to production of fluorobenzene. The technological process for producing fluorobenzene using the traditional hydrogen fluoride method is as follows: aniline is firstly salted in hydrogen fluoride, and then diazotized with dry sodium nitrite, the reaction temperature is controlled to 0~10° C. After the reaction is ended, the diazonium salt solution is thermally decomposed below 40° C. After the thermal decomposition is ended, the thermally decomposed diazonium salt solution is subjected to standing and layering, the separated organic layer is washed with water and alkali, and then distilled with steam to obtain a fluorobenzene crude product. Finally, the fluorobenzene crude product is dehydrated with anhydrous calcium chloride to obtain a fluorobenzene finished product. The yield is about 80%, and all the processes adopt batch kettle operation.

Compared with other industrial fluorobenzene production methods, the traditional hydrogen fluoride method has the advantages of less raw materials consumption per unit product, short production process, low equipment investment, short return cycle, high reaction yield and good product quality (purity >99%), has strong competitiveness, and is a main method for industrial production of fluorobenzene at home and abroad.

Nevertheless, due to a batch kettle type production mode, the traditional hydrogen fluoride process inevitably has the following disadvantages:

(1) Poor production safety: firstly, the holdup of hydrogen fluoride in the production process is huge, and hydrogen fluoride has the characteristics of low boiling point, high volatility, high corrosivity and high toxicity, resulting in great potential safety hazards in the production process; secondly, the diazonium salt is very sensitive to heat, and nitrogen is generated during thermal decomposition. In addition, hydrogen fluoride is fast volatilized due to a low boiling point, so once the temperature rises too fast, it will cause the rapid decomposition of the diazonium salt in the reactor to produce a large amount of volatile gases so that the pressure of a system sharply rises so as to cause serious safety problems and even explosion.

(2) Low reaction yield: at the stage of thermal decomposition, in order to control the thermal decomposition rate and ensure the orderly release of nitrogen, a gradual heating mode is adopted, the whole thermal decomposition of the diazonium salts lasts for 6 hour or more, and a part of the diazonium salts generate side reactions such as hydrolysis and polymerization in the process of long-term heating so as to result in a fact that the reaction yield can only reach about 80%.

(3) A large amount of three wastes and difficult treatment: in the process of long-term thermal decomposition of diazonium salts, a part of the diazonium salts generate side reactions such as hydrolysis and polymerization to generate a large number of tar-like byproducts. These tar-like byproducts can affect the separation and recycle of fluorobenzene, hydrogen fluoride and the like so as to further increase the generation of three wastes, and finally a large amount of fluorine-containing dangerous solid wastes which are extremely difficultly treated are formed.

(4) Poor production environment and inconformity with EHS requirements: due to the batch kettle production mode, the production process cannot be performed under the close condition, volatilization and escape of hydrogen fluoride cannot be avoided to harm operation workers and surrounding environment. Long-term suction of low-concentration hydrogen fluoride can cause chronic poisoning, vomiting, dizziness and other symptoms. When the concentration of HF is more than 30 μg/m$^3$, acute poisoning occurs, and hydrogen fluoride in the atmosphere can also lead to reduction in output of fruit trees and crops, such as ginkgo, apple, barley, corn and rice.

In order to overcome the shortcomings caused by a fact that the traditional batch kettle hydrogen fluoride method is used for the production of fluorobenzene, CN110283039A uses a tubular reactor for thermal decomposition reaction of diazonium salts to replace the traditional kettle thermal decomposition reaction. However, since the tubular reactor is poor in heat exchange, the feeding speed can be slowed and the thermal decomposition time is prolonged to avoid the accumulation of reaction heat, as a result, the thermal decomposition reaction time is still long, the uncontrolled risk of the thermal decomposition reaction still exists, and the occurrence of side reactions cannot be well overcome, that is, the reaction stability is poor. In addition, the salt forming reaction and diazotization reaction of aniline and hydrogen fluoride still use the batch kettle process, so the improvement of the process for producing fluorobenzene by the hydrogen fluoride method is limited. Based on the above technology, CN111116303A uses nitrosylsulfuric acid as a diazotization reagent and adopts a micro-channel reactor made of silicon carbide to realize the continuous diazotization reaction between the hydrofluoric acid solution of the aniline hydrogen fluoride salt and nitrosylsulfuric acid. The diazotization reaction solution enters a pyrolysis reactor for thermal decomposition reaction for 5~60 minutes, and finally a series of posttreatments are carried out to obtain fluorobenzene. The technology adopts the micro-channel reactor made of silicon carbide at the stage of diazotization reaction to solve the continuous problem of diazotization reaction, which is greatly improved compared with the traditional batch kettle hydrogen fluoride method. However, the thermal decomposition reaction of the diazonium salt still uses the tubular reactor, and the thermal decomposition reaction time is still long. In addition, the salt forming reaction of aniline and hydrogen fluoride still adopts the batch kettle operation, there is still large holdup of hydrogen fluoride in the production process, and the safety risk of hydrogen fluoride has not been effectively reduced. The posttreatment adopts the traditional batch mode, which only partially improves the production process of the batch kettle hydrogen fluoride method, and does not fundamentally solve the disadvantages existing in the hydrogen fluoride method. Therefore, for the shortcomings existing in the production process of the hydrogen fluoride method, it is still necessary to consider and study a lot of optimization works.

SUMMARY OF PRESENT INVENTION

In view of this, aiming at the defects in the prior art, the disclosure provides a high-efficiency safe full continuous flow synthesis process of fluorine-containing aromatic hydrocarbon compounds. The process has the advantages of high reaction yield, excellent product quality, good production safety, little pollution discharges and the like, and can achieve continuous production and automatic control of the whole procedure.

The technical solution adopted by the disclosure is as follows:

Provided is a full continuous flow synthesis process of fluorine-containing aromatic hydrocarbon compounds, comprising:

(1) according to a feeding ratio of aromatic amine to hydrogen fluoride, pumping aromatic amine into a thermostat A, pumping hydrogen fluoride into a thermostat B, and keeping the temperatures of the materials constant;

(2) allowing aromatic amine and hydrogen fluoride flowing out from the thermostats to flow into a micro-channel reactor C for a salt forming reaction to obtain a hydrofluoric acid solution of an aromatic amine hydrogen fluoride salt;

(3) according to a feeding ratio of nitrosylsulfuric acid to aromatic amine, pumping a sulfuric acid solution of nitrosylsulfuric acid into a thermostat D, and keeping the temperatures of the materials constant;

(4) allowing the hydrofluoric acid solution of the aromatic amine hydrogen fluoride salt flowing out from the micro-channel reactor C and the sulfuric acid solution of nitrosylsulfuric acid flowing out from the thermostat D to flow into a micro-channel reactor E for a diazotization reaction to obtain an aryl diazonium salt solution;

(5) allowing the aryl diazonium salt solution flowing out from the micro-channel reactor E to flow into a micro-channel reactor F for a thermal decomposition reaction to obtain a mixture consisting of fluorine-containing aromatic hydrocarbons, hydrofluoric acid, sulfuric acid and nitrogen;

(6) allowing the mixture consisting of fluorine-containing aromatic hydrocarbons, hydrofluoric acid, sulfuric acid and nitrogen to flow through a cooler G and then enter a three-phase separator H for continuous separation, discharging nitrogen at a gas outlet of the three-phase separator H, allowing a fluorine-containing aromatic hydrocarbon crude product to flow out from a light liquid phase outlet of the three-phase separator H, and allowing a mixture of hydrofluoric acid and sulfuric acid to flow out from a heavy liquid phase outlet of the three-phase separator H;

(7) spraying the nitrogen discharged from the gas outlet of the three-phase separator H in a spray tower I to remove acid, and then discharging;

(8) allowing the fluorine-containing aromatic hydrocarbon crude product flowing from the light liquid phase outlet of the three-phase separator H to enter a continuous alkaline washing tower J for alkaline washing to remove acid, followed by dehydrating in a continuous drying tower K and rectifying in a continuous rectification tower L, so as to obtain a fluorine-containing aromatic hydrocarbon finished product; and (9) distilling the mixture of hydrofluoric acid and sulfuric acid flowing from the heavy liquid phase outlet of the three-phase separator H in a continuous distillation tower M to obtain recycled hydrogen fluoride and recycled sulfuric acid.

The disclosure can be expressed using the following reaction formula:

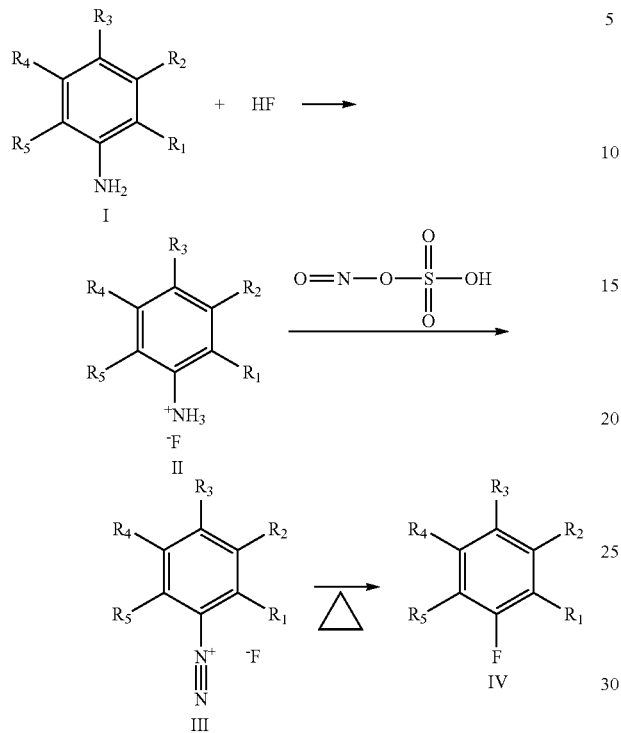

Wherein, $R_1$~$R_5$ are independently selected from H and C1~C3 linear or branched alkyl, respectively.

The disclosure is further set as follows:

The aromatic amine is selected from any one of: aniline, o-methylaniline, m-methylaniline, p-methylaniline, o-ethylaniline, m-ethylaniline, p-ethylaniline, 2,3-dimethylaniline, 2,4-dimethylaniline, 2,5-dimethylaniline, 2,6-dimethylaniline, 3,4-dimethylaniline, 3,5-dimethylaniline, 2,3,4-trimethylaniline, 2,3,5-trimethylaniline, 2,3,6-trimethylaniline, 2,4,5-trimethylaniline, 2,4,6-trimethylaniline, 3,4,5-trimethyl aniline, 2,3,4,5-tetramethylaniline, 2,3,5,6-tetramethylaniline, 2,3,4,6-tetramethylaniline and pentamethylaniline.

The hydrogen fluoride requires the water content that is as low as possible. However, the absolute anhydrous hydrogen fluoride cannot be achieved in the process of practical use. Therefore, the water content of hydrogen fluoride is required to be less than 1.0%, preferably, the water content of hydrogen fluoride is less than 0.5%, more preferably, the water content of hydrogen fluoride is less than 0.2%. Increase in water content of hydrogen fluoride will cause increase in corrosivity of hydrogen fluoride, thereby enlarging the risk of equipment damage due to corrosion. In addition, the water contained in hydrogen fluoride may also trigger a hydrolysis side reaction of diazonium salts in the subsequent diazotization and thermal decomposition reactions so as to cause generation of tar, thereby not only reducing the reaction yield but also increasing the block risk of the micro-channel reactor.

The nitrosylsulfuric acid is a sulfuric acid solution of nitrosylsulfuric acid in which the effective content of nitrosylsulfuric acid is 10%~50%, preferably, the content of nitrosylsulfuric acid is 20%~40%. The sulfuric acid in nitrosylsulfuric acid is only used as a solvent, and nitrosylsulfuric acid, as a diazotization reagent, reacts with aromatic amine to generate a corresponding diazonium salt.

A feeding ratio of aromatic amine to hydrogen fluoride to nitrosylsulfuric acid is as follows: a molar ratio of aromatic amine to hydrogen fluoride to nitrosylsulfuric acid is 1:(5~50):(1~1.2).

The thermostats A, B and C are used for controlling the temperatures of raw materials aromatic amine, hydrogen fluoride and nitrosylsulfuric acid before entering into the micro-channel reactors. The main purposes are as follows:
(1) The temperatures of materials entering the micro-channel reactors are stabilized to avoid the fluctuation of the temperatures of the materials, especially, the temperatures of the materials vary with time, seasons, geographic positions and the like, which facilitates the all-weather all-territory stable operation of a system;
(2) the constant material temperature facilitates the micro-channel reactor to be maintained in a stable state and debugging of the full continuous flow system, and the long-term stable operation of the full system flow is ensured after the debugging is stable. The basic principle of the thermostat is consistent to that of a heat exchanger, which is that the temperature of the material entering the thermostat is adjusted through temperature-adjustable heat exchange mediums isolated from each other, so that the temperature of the material is constant within the required temperature range. After aromatic amine passes through the thermostat A, the temperature of the outlet is controlled to −20~70° C., the temperature fluctuation is as small as possible, and the temperature fluctuation is generally required to be less than ±2° C., preferably less than ±1° C., more preferably less than ±0.5° C.; after hydrogen fluoride passes through thermostat B, the outlet temperature is controlled to −50~20° C., the temperature fluctuation is as small as possible, and the temperature fluctuation is generally required to be less than ±2° C., preferably less than ±1° C., more preferably less than ±0.5° C.; after the sulfuric acid solution of nitrosylsulfuric acid passes through the thermostat D, the temperature is controlled to −30~50° C., the temperature fluctuation is as small as possible, and the temperature fluctuation is generally required to be less than ±2° C., preferably less than ±1° C., more preferably less than ±0.5° C. According to the different properties of the contact materials, the thermostats A, B and C select different materials, wherein because the contact material of the thermostat A is aromatic amine which is low in corrosivity, the material of the thermostat A is wide in selection range, such as silicon carbide, Monel alloy, Hastelloy, 316 L and 304 L. Due to the high corrosivity of the contact material, the materials of the thermostats B and C need to select materials with good corrosion resistance, such as silicon carbide, Monel alloy and Hastelloy.

The micro-channel reactor C is required to have an excellent mixing effect and an excellent heat exchange effect and can timely export the heat generated by the reaction of aromatic amine and hydrogen fluoride to produce the aromatic amine hydrogen fluoride salt, its material is required to withstand the corrosion of hydrofluoric acid, and the selectable materials comprise silicon carbide, Monel and Hastelloy. The temperature of the material at the outlet of the micro-channel reactor C is controlled to −10~20° C., the temperature fluctuation is as small as possible, the temperature fluctuation is generally required to be less than ±2° C., preferably less than ±1° C., more preferably less than ±0.5°

C. In the micro-channel reactor C, aromatic amine reacts with hydrogen fluoride to generate the aromatic amine hydrogen fluoride salt which is dissolved into excess hydrofluoric acid to form a hydrofluoric acid solution of an aromatic amine hydrogen fluoride salt, and the hydrofluoric acid solution of the aromatic amine hydrogen fluoride salt flows out from the outlet of micro-channel reactor C and then enters the micro-channel reactor E.

The micro-channel reactor E is required to have a good mixing effect and an excellent heat exchange effect and can timely export heat generated by diazotization reaction of the aromatic amine hydrogen fluoride salt and nitrosylsulfuric acid, and the material of the micro-channel reactor E is required to withstand the corrosion of hydrofluoric acid and sulfuric acid, and the selectable materials comprise silicon carbide, Monel and Hastelloy. The temperature of the material in the micro-channel reactor E is controlled to −20~20° C., the temperature of the material at the outlet is controlled to −20~20° C., the temperature fluctuation is as small as possible, and the temperature fluctuation is generally required to be less than ±2° C., preferably the temperature fluctuation is less than ±2° C., more preferable the temperature fluctuation is less than =0.5° C. In the micro-channel reactor E, the aromatic amine hydrogen fluoride salt reacts with nitrosylsulfuric acid to generate an aryl diazonium salt, the aryl diazonium salt is dissolved into excess hydrofluoric acid to form the hydrofluoric acid solution of the diazonium salt, and the hydrofluoric acid solution of the diazonium salt flows out from the outlet of the micro-channel reactor E and then enters the micro-channel reactor F.

The micro-channel reactor F is required to have a good mixing effect and an excellent heat exchange effect and can timely export heat generated in the thermal decomposition process of the diazonium salt, and the material of the micro-channel reactor F is required to withstand the corrosion of hydrofluoric acid and sulfuric acid, and the selectable materials comprise silicon carbide, Monel and Hastelloy. The temperature of the material in the micro-channel reactor F is controlled to 20~100° C., the temperature of the material at the outlet is controlled to 20~100° C., and the temperature fluctuation is as small as possible. In the micro-channel reactor F, the aryl diazonium salt is thermally decomposed to generate a mixture consisting of fluorine-containing aromatic hydrocarbon, hydrofluoric acid, sulfuric acid, nitrogen and the like, and the mixture flows out from the outlet of the micro-channel reactor F and then enters the cooler G.

The cooler G is required to have an excellent heat exchange effect and can rapidly cool the mixture consisting of fluorine-containing aromatic hydrocarbon, hydrofluoric acid, sulfuric acid and nitrogen formed by thermal decomposition, thereby avoiding volatilization of liquid with a low boiling point excluding nitrogen. The material of the cooler G is required to withstand the corrosion of hydrofluoric acid and sulfuric acid, and the selectable materials comprise silicon carbide, Monel and Hastelloy. The temperature of the material at the outlet of the cooler G is controlled to −20~20° C. The mixture consisting of fluorine-containing aromatic hydrocarbon, hydrofluoric acid, sulfuric acid and nitrogen is cooled in the cooler G and then enters the three-phase separator F.

The three-phase separator H is required to ensure that a gas phase formed by nitrogen, a light liquid phase formed by fluorine-containing aromatic hydrocarbon and a heavy liquid phase formed by hydrofluoric acid and sulfuric acid are sufficiently separated and flow out from the different positions of the three-phase separator H according to the different densities of the three phases, wherein nitrogen, as a gas phase component, is discharged from the gas outlet of the three-phase separator H, the light liquid phase formed by fluorine-containing aromatic hydrocarbons flows out from the light liquid phase outlet of the three-phase separator H, the heavy liquid phase formed by hydrofluoric acid and sulfuric acid flows out from the heavy liquid phase outlet of the three-phase separator H, thereby achieving the continuous separation of the three phases. The three-phase separator H can adopt a horizontal structure or a vertical structure, the material of the three-phase separator H is required to withstand the corrosion of hydrofluoric acid and sulfuric acid, and the selectable materials comprise silicon carbide, Monel, Hastelloy and PTFE. The temperature of the material in the three-phase separator H is controlled to −20~20° C.

The nitrogen discharged from the outlet of the three-phase separator H contains a few amount of hydrofluoric acid, and the entrained hydrofluoric acid is removed by using a method of removing acid via spraying in a spray tower I so that nitrogen meets a direct discharge standard. The spray manner of the spray tower I can select single-stage alkaline solution spray or multi-stage alkaline solution spray, or comprehensive water and alkaline solution spray, etc. The spray tower can be a packed tower or a plate tower. The used alkaline solution is an aqueous solution of inorganic alkali, and the inorganic alkali can be selected from one or more of sodium hydroxide, potassium hydroxide, sodium carbonate and potassium carbonate, and the pH value of the alkaline solution is required to be more than 9. The operation temperature of the spray tower I is a normal temperature.

The fluorine-containing aromatic hydrocarbon crude product flowing out from the light liquid phase outlet of the three-phase separator H entrains a few amount of hydrofluoric acid and sulfuric acid which can be removed by a manner of removing acid via alkaline washing in a continuous alkaline tower J, then is dehydrated in the continuous drying tower K and finally rectified in a continuous rectification tower L to obtain the fluorine-containing aromatic hydrocarbon finished product. The acid is removed via alkaline washing in the continuous alkaline washing tower J, the alkaline solution enters from the upper part of the alkaline washing tower by using a liquid phase countercurrent manner and flows out from the bottom of the alkaline washing tower via two-phase separation, and the fluorine-containing aromatic hydrocarbon crude product enters from the lower part of the alkaline washing tower and flows out from the top of the alkaline washing tower via two-phase separation; the used alkaline solution is an aqueous solution of the inorganic alkali, the inorganic alkali is selected from one or more of sodium hydroxide, potassium hydroxide, sodium carbonate and potassium carbonate, and the pH value of the alkaline solution is required to be more than 9; the operation temperature of the spray tower I is a normal temperature. The dehydration is carried out in the continuous drying tower K, a dehydration molecular sieve is loaded in the drying tower, and the fluorine-containing aromatic hydrocarbon crude product enters from the bottom of the drying tower, passes through the dehydration molecular sieve and flows out from the upper part of the drying tower; the operation temperature is a normal temperature. The rectification is carried out in the continuous rectification tower L, the rectification tower can be the packed tower or the plate tower, the rectification manner is normal-pressure rectification, and the fraction on the top is condensed to obtain the fluorine-containing aromatic hydrocarbon finished product.

The mixture of hydrofluoric acid and sulfuric acid flowing out from the heavy liquid phase outlet of the three-phase separator H enters the continuous distillation tower M to be distilled, the distillation tower can be the packed tower or plate tower, the material of the distillation tower is required to withstand the corrosion of hydrofluoric acid and sulfuric acid, and the selectable materials comprise silicon carbide, Monel, Hastelloy and PTFE. The distillation manner adopts normal-pressure distillation, the fraction on the top is condensed to obtain received hydrofluoric acid, and the concentrate at the bottom is recycled sulfuric acid. The recycled hydrofluoric acid can be circularly used in the salt forming reaction.

Based on a main raw material aromatic amine, by using the full continuous flow synthesis process of the fluorine-containing aromatic hydrocarbon compounds of the disclosure is adopted, the fluorine-containing aromatic hydrocarbons have a yield of 90% or more and a purity of 99.9% or more, in which the yields of partial fluorine-containing aromatic hydrocarbons such as fluorobenzene and p-fluorotoluene can reach 95% or more.

Compared with the prior art, the full continuous flow synthesis process of the fluorine-containing aromatic hydrocarbon compounds provided by the disclosure has the following main innovation points:

(1) the temperatures of raw materials aromatic amine, hydrogen fluoride and nitrosylsulfuric acid are controlled to proper temperatures in the thermostats and then these raw materials enter the micro-channel reactor, thereby avoiding the heat shock of raw material temperatures on the full continuous flow system and ensuring the stable operation of the system;

(2) the micro-channel reactor is firstly created to perform salt forming reaction of aromatic amine and hydrogen fluoride, so as to realize the continuous proceeding of the salt forming procedures, which avoids that hydrogen fluoride is volatilized due to local overheating triggered by unsmooth heat dissipation when in traditional kettle type salt forming reaction and avoids the defects such as slow salt formation process and low equipment efficiency, more importantly, supplements the shortcomings and lays the foundation for the realization of the full continuous flow production process of the fluorine-containing aromatic hydrocarbon compounds;

(3) in the thermal decomposition reaction, the micro-channel reactor is used to replace the traditional reactors and tubular reactors so as to realize better mixing effect, better heat transfer efficiency and less holdup, thereby greatly improving the safety, environmental protection property of the thermal decomposition reaction and improves the reaction yield;

(4) the continuous production of the full production processes comprising raw material feeding, material constant temperature, salt forming reaction, diazotization reaction, thermal decomposition, material separation and product purification is achieved by using a manner of combining new and old processes and new and old equipment on the basis of the latest micro-channel reactors in combination with traditional technologies such as a continuous three-phase separator, continuous spray, continuous washing and continuous rectification;

(5) after the full continuous flow fluorine-containing aromatic hydrocarbon production process is used, the whole production process adopts micro-channel reactors and a full-closed reaction system, thereby reducing the holdup of hydrogen fluoride and fugitive volatilization of hydrogen fluoride in the production equipment to the greatest extent, fundamentally solving the safety problem existing when fluorine-containing aromatic hydrocarbon compounds are produced using a hydrogen fluoride method, greatly promoting the EHS standard of the production process and facilitating the popularization of the method of producing fluorine-containing aromatic hydrocarbon compounds using the hydrogen fluoride method.

Next, the disclosure will be further described in combination with drawings and specific embodiments. It is noted that the following embodiments are only for helping understanding the disclosure, but do not constitute the limitation of the disclosure. It is impossible for the specific embodiments to use all the technical features of the disclosure. As long as the technical features involved in the Description do not conflict with each other, they can be combined with each other to form new embodiments.

DESCRIPTION OF THE DRAWINGS

FIG. 1 is a diagram of a process flowchart in the present application.

DETAILED DESCRIPTION OF PREFERRED EMBODIMENTS

Basic Examples

A full continuous flow synthesis process of fluorine-containing aromatic hydrocarbon compounds, as shown in FIG. 1, has an equipment list and operation processes:

TABLE 1

| | | | Equipment list |
|---|---|---|---|
| Number | Equipment name | Material | Introduction |
| 1 | Thermostat A | 316L | High-efficiency plate heat exchanger with a material channel holdup volume of 100 mL |
| 2 | Thermostat B | Silicon carbide | High-efficiency plate heat exchanger with a material channel holdup volume of 800 mL |
| 3 | Micro-channel reactor C | Silicon carbide | Three-layer structure, a middle layer is a material channel with a high-efficiency mixing structure and is used for material reaction, and two side layers are used to circulate a heat exchange medium to control the temperature of the material in the middle layer. Material channel holdup volume 1000 mL |
| 4 | Thermostat D | HC276 | High-efficiency plate heat exchanger with a material channel holdup volume 500 mL |

TABLE 1-continued

Equipment list

| Equipment Number | Equipment name | Material | Introduction |
|---|---|---|---|
| 5 | Micro-channel reactor E | Silicon carbide | Three-layer structure, a middle layer is a material channel with a high-efficiency mixing structure and is used for material reaction, and two side layers are used to circulate a heat exchange medium to control the temperature of the material in the middle layer. Material channel holdup volume 2000 mL |
| 6 | Micro-channel reactor F | Silicon carbide | Three-layer structure, a middle layer is a material channel with a high-efficiency mixing structure and is used for material reaction, and two side layers are used to circulate a heat exchange medium to control the temperature of the material in the middle layer. Material channel holdup volume 2000 mL |
| 7 | Cooler G | Silicon carbide | High-efficiency plate heat exchanger with a material channel holdup volume 2000 mL |
| 8 | Three-phase separator H | 316 lining PTFE | Vertical structure, diameter 100 mm, height 1200 mm, holdup volume 9000 mL |
| 9 | Spray tower I | 316L | Two-stage series alkaline spraying, single tower diameter 200 mm, height 1500 mm, filled with ring-shaped PTFE filler loaded inside |
| 10 | Continuous alkaline washing tower J | 316L | Diameter 120 mm, height 1500 mm, 800 mm ring PTFE packing loaded inside |
| 11 | Continuous rectification tower K | 316L | Three towers are connected in parallel, one for use, one for standby and one for activation. Single tower has a diameter of 120 mm and a height of 2000 mm, and is filled with a 3A molecular sieve having a height of 1500 mm |
| 12 | Continuous rectification tower L | 316L | Heating a tower kettle with a diameter of 80 mm, a height of 1500 mm, and 1000 mm stainless steel wire mesh packing loaded inside |
| 13 | Continuous rectification tower M | Monel | Heating a tower kettle with a diameter of 100 mm, a height of 1600 mm, and 1000 mm ring PTFE filler loaded inside |

Operation Processes:

(1) Aromatic hydrocarbons are metered with a metering pump and then pumped into a thermostat A at the flow rate of 10~100 g/min, after that, the temperature of an outlet is controlled to −20~70° C., and the temperature fluctuation is less than ±0.5° C.

(2) Hydrogen fluoride is metered with a metering pump and then pumped into a thermostat B at the flow rate of 10~900 g/min, after that, the temperature of an outlet is controlled to −50~20° C., and the temperature fluctuation is less than ±0.5° C.

(3) Aromatic amine and hydrogen fluoride flowing out from the thermostats A and B immediately flow into a micro-channel reactor C, a salt forming reaction is carried out to obtain an aromatic amine hydrogen fluoride salt solution, and the temperature of the outlet of the micro-channel reactor C is controlled −10~20° C., and the temperature fluctuation is less than ±0.5° C.

(4) A sulfuric acid solution of nitrosylsulfuric acid is metered with a metering pump and then pumped into a thermostat D at the flow rate of 10~800 g/min, after that, the temperature of the outlet is controlled to −30~50° C., and the temperature fluctuation is less than ±0.5° C.

(5) The aromatic amine hydrogen fluoride salt solution flowing out from the micro-channel reactor C together with the sulfuric acid solution of nitrosylsulfuric acid flowing out from the thermostat D flows into a micro-channel reactor E for diazotization reaction, the temperatures of the materials in the reactor are controlled to −20~20° C., the temperatures of the materials at the outlet are controlled to −20~20° C., and the temperature fluctuation is less than ±0.5° C.

(6) an aryl diazonium salt solution flowing out from the micro-channel reactor E flows into a micro-channel reactor F for thermal decomposition, the temperatures of the materials in the reactor are controlled to 20~100° C., the temperatures of the materials at the outlet are controlled to 20~100° C., the temperature fluctuation is less than ±2° C., and a mixture consisting of fluorine-containing aromatic hydrocarbons, hydrofluoric acid, sulfuric acid and nitrogen is obtained.

(7) The mixture consisting of fluorine-containing aromatic hydrocarbons, hydrofluoric acid, sulfuric acid and nitrogen flowing out from the micro-channel reactor F passes through a cooler G, and the temperature of the outlet is controlled to −20~20° C.

(8) The mixture consisting of fluorine-containing aromatic hydrocarbons, hydrofluoric acid, sulfuric acid and nitrogen flowing out from the cooler G enters a three-phase separator H for continuous separation, nitrogen is discharged from the outlet on the top of the three-phase separator H, a fluorine-containing aromatic hydrocarbon crude product flows out from the light liquid outlet on the upper part of the three-phase separator H, a mixture of hydrofluoric acid and sulfuric acid flows out from the heavy liquid phase outlet at the bottom of the three-phase separator H, and the temperatures of the materials in the three-phase separator H are controlled to −20~20° C.

(9) Nitrogen discharged from the outlet on the top of the three-phase separator H is sprayed in a spray tower I to remove acid and then discharged. The spray tower I selects a two-stage series alkaline spray tower, its structure adopts a packed tower form, a circular PTFE filler is filled inside, the alkaline solution used for spraying is a potassium hydroxide solution, the pH value is controlled to more than 9, and the operation temperature is room temperature.

(10) The fluorine-containing crude product flowing out from the light liquid phase outlet on the upper part of the three-phase separator H passes through a continuous alkaline washing tower J to remove acid, then is dehydrated in a continuous drying tower K and rectified in continuous rectification tower L to obtain a fluorine-containing aromatic hydrocarbon finished product. The continuous alkaline washing tower J is a packed tower, a liquid-phase countercurrent manner is adopted, the alkaline solution enters from the upper part of the alkaline washing tower and then flows out from the bottom of the alkaline washing tower via two-phase separation, the fluorine-containing aromatic hydrocarbon crude product enters from the lower part of the alkaline washing tower and flows out from the top of the alkaline washing tower via two-phase separation, and the operation temperature is a normal temperature; the continuous drying tower K is a packed tower inside a 3 A molecular sieve is loaded, a three-tower form is adopted, one is used, one is used for standby, and one is used for activation, and flexible switching occurs among the three towers. The fluorine-containing aromatic hydrocarbon crude product enters from the lower part of the drying tower and flows out from the drying tower, and the operation temperature is a normal temperature; the continuous rectification tower L adopts the packed tower in which stainless steel cloth fillers, the tower kettle is heated rectification is conducted at a normal pressure, the fraction on the top is condensed to obtain a fluorine-containing aromatic hydrocarbon finished product.

(11) The mixture of hydrofluoric acid and sulfuric acid flowing out from the heavy liquid phase outlet at the bottom of the three-phase separator H is distilled in a continuous distillation tower M, the fraction on the top is condensed to obtain recycled hydrofluoric acid, and the concentrate from the tower kettle is recycled sulfuric acid; the continuous rectification tower M adopts the packed tower in which the circular PTFE filler is loaded, the tower kettle is heated, and distillation is conducted at normal pressure.

Next, parameters in the implementation process of this solution, such as raw material types, flow rates and temperatures, will be specifically researched.

Example 1

This example is full continuous flow synthesis of fluorobenzene, in combination with FIG. 1, comprising the following specific steps:

(1) aniline was metered with a metering pump and then pumped into a thermostat A at the flow rate of 50 g/min, after that, the temperature of an outlet was controlled to 5±0.5° C.;

(2) hydrogen fluoride was metered with a metering pump and then pumped into a thermostat B at the flow rate of 215 g/min, after that, the temperature of an outlet was controlled to −10±0.5° C.;

(3) aniline and hydrogen fluoride flowing out from the thermostats A and B immediately flowed into a micro-channel reactor C to be subjected to a salt forming reaction to obtain a hydrofluoric acid solution of an aniline hydrogen fluoride salt, and the temperature of the outlet of the micro-channel reactor C was controlled to 0±0.5° C.;

(4) a sulfuric acid solution of 40% nitrosylsulfuric acid was metered with a metering pump and then pumped into a thermostat D at the flow rate of 181 g/min, after that, the temperature of the outlet was controlled to 0±0.5° C.;

(5) the hydrofluoric acid solution of the aniline hydrogen fluoride salt flowing out from the micro-channel reactor C together with the sulfuric acid solution of nitrosylsulfuric acid flowing out from the thermostat D flowed into a micro-channel reactor E for diazotization reaction, the temperature of the diazotization reaction was controlled to 5~10° C., the temperature of the material at the outlet was controlled to 10±0.5° C., and a phenyl diazonium salt solution was obtained;

(6) the phenyl diazonium salt solution flowing out from the micro-channel reactor E flowed into a micro-channel reactor F for thermal decomposition, the temperature of thermal decomposition was controlled to 70±2° C., and a mixture consisting of fluorobenzene, hydrofluoric acid, sulfuric acid and nitrogen was obtained at the outlet;

(7) the mixture consisting of fluorobenzene, hydrofluoric acid, sulfuric acid and nitrogen flowing out from the micro-channel reactor F flowed into a cooler G for cooling, and the temperature of the outlet of the cooler G was controlled to 5~10° C.;

(8) the mixture consisting of fluorine-containing aromatic hydrocarbons, hydrofluoric acid, sulfuric acid and nitrogen flowing out from the cooler G entered a three-phase separator H for continuous separation, nitrogen was discharged from the outlet on the top of the three-phase separator H, a fluorobenzene crude product flowed out from the light liquid outlet on the upper part of the three-phase separator H, a mixture of hydrofluoric acid and sulfuric acid flowed out from the heavy liquid phase outlet at the bottom of the three-phase separator H, and the temperatures of the materials in the three-phase separator H were controlled to 5~10° C.;

(9) nitrogen discharged from the outlet on the top of the three-phase separator H was sprayed in a two-stage series spray tower I to remove acid and then discharged, and the operation temperature of the spray tower I was room temperature;

(10) the fluorobenzene crude product flowing out from the light liquid outlet on the upper part of the three-phase separator H was subjected to alkaline washing in a continuous alkaline washing tower J to remove acid, then dehydrated in a continuous drying tower K and rectified in a continuous rectification tower L to obtain a fluorobenzene finished product; and

(11) a mixture of hydrofluoric acid and sulfuric acid flowing out from the heavy liquid phase outlet at the bottom of the three-phase separator H was distilled in a continuous distillation tower M, the fraction on the top was condensed to obtain recycled hydrofluoric acid, and the concentrate from the tower kettle was recycled sulfuric acid.

The efficient continuous flow synthesis process of fluorobenzene in this example consumed for 12 hours starting from feeding to stable debugging. Timing was conducted after debugging was accomplished, and this process stably operated for 300 hours. The results are summarized as follows: 900 kg of aniline, 3870 kg of hydrofluoric acid and 3258 kg of 40% nitrosylsulfuric acid solution are totally consumed; 918.5 kg of fluorobenzene finished product is obtained, with a yield of 98.9% and a purity of 99.97%.

Example 2

This example is full continuous flow synthesis of p-methyl fluorobenzene, in combination with FIG. 1, comprising the following specific steps:
(1) p-toluidine was metered with a metering pump and then pumped into a thermostat A at the flow rate of 60 g/min, after that, the temperature of an outlet was controlled to 55±0.5° C.;
(2) hydrogen fluoride was metered with a metering pump and then pumped into a thermostat B at the flow rate of 168 g/min, after that, the temperature of an outlet was controlled to −20±0.5° C.;
(3) p-toluidine and hydrogen fluoride flowing out from the thermostats A and B immediately flowed into a micro-channel reactor C to be subjected to a salt forming reaction to obtain a hydrofluoric acid solution of an p-toluidine hydrogen fluoride salt, and the temperature of the outlet of the micro-channel reactor C was controlled to 10±0.5° C.;
(4) a sulfuric acid solution of 30% nitrosylsulfuric acid was metered with a metering pump and then pumped into a thermostat D at the flow rate of 250 g/min, after that, the temperature of the outlet was controlled to −5±0.5° C.;
(5) the hydrofluoric acid solution of the p-toluidine hydrogen fluoride salt flowing out from the micro-channel reactor C together with the sulfuric acid solution of nitrosylsulfuric acid flowing out from the thermostat D flowed into a micro-channel reactor E for diazotization reaction, the temperature of the diazotization reaction was controlled to 0~5° C., the temperature of the material at the outlet was controlled to 5±0.5° C., and a p-methylphenyl diazonium salt solution was obtained;
(6) the p-methylphenyl diazonium salt solution flowing out from the micro-channel reactor E flowed into a micro-channel reactor F for thermal decomposition, the temperature of thermal decomposition was controlled to 60±2° C., and a mixture consisting of p-methyl fluorobenzene, hydrofluoric acid, sulfuric acid and nitrogen was obtained at the outlet;
(7) the mixture consisting of p-methyl fluorobenzene, hydrofluoric acid, sulfuric acid and nitrogen flowing out from the micro-channel reactor F flowed into a cooler G for cooling, and the temperature of the outlet of the cooler G was controlled to 0~5° C.;
(8) the mixture consisting of p-methyl fluorobenzene, hydrofluoric acid, sulfuric acid and nitrogen flowing out from the cooler G entered a three-phase separator H for continuous separation, nitrogen was discharged from the outlet on the top of the three-phase separator H, a p-methyl fluorobenzene crude product flowed out from the light liquid outlet on the upper part of the three-phase separator H, a mixture of hydrofluoric acid and sulfuric acid flowed out from the heavy liquid phase outlet at the bottom of the three-phase separator H, and the temperatures of the materials in the three-phase separator H were controlled to 0~5° C.;
(9) nitrogen discharged from the outlet on the top of the three-phase separator H was sprayed in a two-stage series spray tower I to remove acid and then discharged, and the operation temperature of the spray tower I was room temperature;
(10) the p-methyl fluorobenzene crude product flowing out from the light liquid outlet on the upper part of the three-phase separator H was subjected to alkaline washing in a continuous alkaline washing tower J to remove acid, then dehydrated in continuous drying tower K and rectified in continuous rectification tower L to obtain a p-methyl fluorobenzene finished product; and
(11) a mixture of hydrofluoric acid and sulfuric acid flowing out from the heavy liquid phase outlet at the bottom of the three-phase separator H was distilled in a continuous distillation tower M, the fraction on the top was condensed to obtain recycled hydrofluoric acid, and the concentrate from the tower kettle was recycled sulfuric acid.

The efficient continuous flow synthesis process of p-methyl fluorobenzene in this example consumed for 15 hours starting from feeding to stable debugging. Timing was conducted after debugging was accomplished, and this process stably operated for 300 hours. The results are summarized as follows: 1080 kg of p-methylaniline, 3024 kg of hydrofluoric acid and 4500 kg of 30% nitrosylsulfuric acid solution are totally consumed; 1093.4 kg of p-methyl fluorobenzene finished product is obtained, with a yield of 98.5% and a purity of 99.93%.

Example 3

This example is full continuous flow synthesis of o-methyl fluorobenzene, in combination with FIG. 1, comprising the following specific steps:
(1) o-toluidine was metered with a metering pump and then pumped into a thermostat A at the flow rate of 80 g/min, after that, the temperature of an outlet was controlled to 15±0.5° C.;
(2) hydrogen fluoride was metered with a metering pump and then pumped into a thermostat B at the flow rate of 150 g/min, after that, the temperature of an outlet was controlled to −15±0.5° C.;
(3) o-toluidine and hydrogen fluoride flowing out from the thermostats A and B immediately flowed into a micro-channel reactor C to obtain a hydrofluoric acid solution of an o-toluidine hydrogen fluoride salt through salt forming reaction, and the temperature of the outlet of the micro-channel reactor C was controlled to −3±0.5° C.;
(4) a sulfuric acid solution of 20% nitrosylsulfuric acid was metered with a metering pump and then pumped into a thermostat D at the flow rate of 485 g/min, after that, the temperature of the outlet was controlled to 5±0.5° C.;
(5) the hydrofluoric acid solution of the o-toluidine hydrogen fluoride salt flowing out from the micro-channel reactor C together with the sulfuric acid solution of nitrosylsulfuric acid flowing out from the thermostat D flowed into a micro-channel reactor E for diazotization reaction, the temperature of the diazotization reaction was controlled to −5~0° C., the temperature of the material at the outlet was controlled to 0±0.5° C., and an o-methylphenyl diazonium salt solution was obtained;
(6) the o-methylphenyl diazonium salt solution flowing out from the micro-channel reactor E flowed into micro-channel reactor F for thermal decomposition, the temperature of thermal decomposition was controlled to 50±2° C., and a mixture consisting of o-methyl fluorobenzene, hydrofluoric acid, sulfuric acid and nitrogen was obtained at the outlet;

(7) the mixture consisting of o-methyl fluorobenzene, hydrofluoric acid, sulfuric acid and nitrogen flowing out from the micro-channel reactor F flowed into a cooler G for cooling, and the temperature of the outlet of the cooler G was controlled to 0~5° C.;

(8) the mixture consisting of o-methyl fluorobenzene, hydrofluoric acid, sulfuric acid and nitrogen flowing out from the cooler G entered a three-phase separator H for continuous separation, nitrogen was discharged from the outlet on the top of the three-phase separator H, an o-methyl fluorobenzene crude product flowed out from the light liquid outlet on the upper part of the three-phase separator H, a mixture of hydrofluoric acid and sulfuric acid flowed out from the heavy liquid phase outlet at the bottom of the three-phase separator H, and the temperature of the materials in the three-phase separator H was controlled to 0~5° C.;

(9) nitrogen discharged from the outlet on the top of the three-phase separator H was sprayed in a two-stage series spray tower I to remove acid and then discharged, and the operation temperature of the spray tower I was room temperature;

(10) the o-methyl fluorobenzene crude product flowing out from the light liquid outlet on the upper part of the three-phase separator H was subjected to alkaline washing in a continuous alkaline washing tower J to remove acid, then dehydrated in continuous drying tower K and rectified in a continuous rectification tower L to obtain an o-methyl fluorobenzene finished product; and

(11) a mixture of hydrofluoric acid and sulfuric acid flowing out from the heavy liquid phase outlet at the bottom of the three-phase separator H was distilled in a continuous distillation tower M, the fraction on the top was condensed to obtain recycled hydrofluoric acid, and the concentrate from the tower kettle was recycled sulfuric acid.

The efficient continuous flow synthesis process of o-toluidine in this example consumed for 15 hours starting from feeding to stable debugging. Timing was conducted after debugging was accomplished, and this process stably operated for 300 hours. The results are summarized as follows: 1440 kg of o-methyl fluorobenzene, 2700 kg of hydrofluoric acid and 8730 kg of 20% nitrosylsulfuric acid solution are totally consumed; 1451.9 kg of o-methyl fluorobenzene finished product is obtained, with a yield of 98.1% and a purity of 99.91%.

Example 4

This example is full continuous flow synthesis of m-methyl fluorobenzene, in combination with FIG. 1, comprising the following specific steps:

(1) m-methylaniline was metered with a metering pump and then pumped into a thermostat A at the flow rate of 70 g/min, after that, the temperature of an outlet was controlled to −5±0.5° C.;

(2) hydrogen fluoride was metered with a metering pump and then pumped into a thermostat B at the flow rate of 157 g/min, after that, the temperature of an outlet was controlled to 0±0.5° C.;

(3) m-methylaniline and hydrogen fluoride flowing out from the thermostats A and B immediately flowed into a micro-channel reactor C to be subjected to a salt forming reaction to obtain a hydrofluoric acid solution of an m-methylaniline hydrogen fluoride salt, and the temperature of the outlet of the micro-channel reactor C was controlled to 0±0.5° C.;

(4) a sulfuric acid solution of 25% nitrosylsulfuric acid was metered with a metering pump and then pumped into a thermostat D at the flow rate of 359 g/min, after that, the temperature of the outlet was controlled to 2±0.5° C.;

(5) the hydrofluoric acid solution of the m-methylaniline hydrogen fluoride salt flowing out from the micro-channel reactor C together with the sulfuric acid solution of nitrosylsulfuric acid flowing out from the thermostat D flowed into a micro-channel reactor E for diazotization reaction, the temperature of the diazotization reaction was controlled to −2~2° C., the temperature of the material at the outlet was controlled to 2±0.5° C., and an m-methylphenyl diazonium salt solution was obtained;

(6) the m-methylphenyl diazonium salt solution flowing out from the micro-channel reactor E flowed into a micro-channel reactor F for thermal decomposition, the temperature of thermal decomposition was controlled to 40±2° C., and a mixture consisting of m-methylaniline, hydrofluoric acid, sulfuric acid and nitrogen was obtained at the outlet;

(7) the mixture consisting of m-methylaniline, hydrofluoric acid, sulfuric acid and nitrogen flowing out from the micro-channel reactor F flowed into a cooler G for cooling, and the temperature of the outlet of the cooler G was controlled to 0~10° C.;

(8) the mixture consisting of m-methylaniline, hydrofluoric acid, sulfuric acid and nitrogen flowing out from the cooler G entered a three-phase separator H for continuous separation, nitrogen was discharged from the outlet on the top of the three-phase separator H, an m-methylaniline crude product flowed out from the light liquid outlet on the upper part of the three-phase separator H, a mixture of hydrofluoric acid and sulfuric acid flowed out from the heavy liquid phase outlet at the bottom of the three-phase separator H, and the temperatures of the materials in the three-phase separator H were controlled to 0~10° C.;

(9) nitrogen discharged from the outlet on the top of the three-phase separator H was sprayed in a two-stage series spray tower I to remove acid and then discharged, and the operation temperature of the spray tower I was room temperature;

(10) the m-methylaniline crude product flowing out from the light liquid outlet on the upper part of the three-phase separator H was subjected to alkaline washing in a continuous alkaline washing tower J to remove acid, then dehydrated in continuous drying tower K and rectified in continuous rectification tower L to obtain an m-methylaniline finished product; and

(11) a mixture of hydrofluoric acid and sulfuric acid flowing out from the heavy liquid phase outlet at the bottom of the three-phase separator H was distilled in a continuous distillation tower M, the fraction on the top was condensed to obtain recycled hydrofluoric acid, and the concentrate from the tower kettle was recycled sulfuric acid.

The efficient continuous flow synthesis process of m-methyl fluorobenzene in this example consumed for 15 hours starting from feeding to stable debugging. Timing was conducted after debugging was accomplished, and this process stably operated for 300 hours. The results are summarized as follows: 1260 kg of m-methylaniline, 2826 kg of hydrofluoric acid and 6462 kg of 25% nitrosylsulfuric acid solution are totally consumed; 1451.9 kg of m-methyl fluorobenzene finished product is obtained, with a yield of 98.3% and a purity of 99.94%.

Example 5

This example is full continuous flow synthesis of 3,5-dimethyl fluorobenzene in combination with FIG. 1, comprising the following specific steps:
(1) 3,5-dimethylaniline was metered with a metering pump and then pumped into a thermostat A at the flow rate of 40 g/min, after that, the temperature of an outlet was controlled to 60±0.5° C.;
(2) hydrogen fluoride was metered with a metering pump and then pumped into a thermostat B at the flow rate of 198 g/min, after that, the temperature of an outlet was controlled to −30±0.5° C.;
(3) 3,5-dimethylaniline and hydrogen fluoride flowing out from the thermostats A and B immediately flowed into a micro-channel reactor C to be subjected to a salt forming reaction to obtain a hydrofluoric acid solution of a 3,5-dimethylaniline hydrogen fluoride salt, and the temperature of the outlet of the micro-channel reactor C was controlled to 5±0.5° C.;
(4) a sulfuric acid solution of 35% nitrosylsulfuric acid was metered with a metering pump and then pumped into a thermostat D at the flow rate of 132 g/min, after that, the temperature of the outlet was controlled to −3±0.5° C.;
(5) the hydrofluoric acid solution of the 3,5-dimethylaniline hydrogen fluoride salt flowing out from the micro-channel reactor C together with the sulfuric acid solution of nitrosylsulfuric acid flowing out from the thermostat D flowed into a micro-channel reactor E for diazotization reaction, the temperature of the diazotization reaction was controlled to −10~−5° C., the temperature of the material at the outlet was controlled to −5±0.5° C., and an 3.5-dimethylphenyl diazonium salt solution was obtained;
(6) the 3,5-dimethylphenyl diazonium salt solution flowing out from the micro-channel reactor E flowed into a micro-channel reactor F for thermal decomposition, the temperature of thermal decomposition was controlled to 80±2° C., and a mixture consisting of 3,5-dimethyl fluorobenzene, hydrofluoric acid, sulfuric acid and nitrogen was obtained at the outlet;
(7) the mixture consisting of 3,5-dimethyl fluorobenzene, hydrofluoric acid, sulfuric acid and nitrogen flowing out from the micro-channel reactor F flowed into a cooler G for cooling, and the temperature of the outlet of the cooler G was controlled to 0~5° C.;
(8) the mixture consisting of 3,5-dimethyl fluorobenzene, hydrofluoric acid, sulfuric acid and nitrogen flowing out from the cooler G entered a three-phase separator H for continuous separation, nitrogen was discharged from the outlet on the top of the three-phase separator H, a 3,5-dimethyl fluorobenzene crude product flowed out from the light liquid outlet on the upper part of the three-phase separator H, a mixture of hydrofluoric acid and sulfuric acid flowed out from the heavy liquid phase outlet at the bottom of the three-phase separator H, and the temperature of the materials in the three-phase separator H was controlled to 5~10° C.;
(9) nitrogen discharged from the outlet on the top of the three-phase separator H was sprayed in a two-stage series spray tower I to remove acid and then discharged, and the operation temperature of the spray tower I was room temperature;
(10) the 3,5-dimethyl fluorobenzene crude product flowing out from the light liquid outlet on the upper part of the three-phase separator H was subjected to alkaline washing in a continuous alkaline washing tower J to remove acid, then dehydrated in continuous drying tower K and rectified in continuous rectification tower L to obtain a fluorobenzene finished product; and
(11) a mixture of hydrofluoric acid and sulfuric acid flowing out from the heavy liquid phase outlet at the bottom of the three-phase separator H was distilled in continuous distillation tower M, the fraction on the top was condensed to obtain recycled hydrofluoric acid to be used for salt forming reaction, and the concentrate from the tower kettle was recycled sulfuric acid.

The efficient continuous flow synthesis process of 3,5-dimethyl fluorobenzene in this example consumed for 20 hours starting from feeding to stable debugging. Timing was conducted after debugging was accomplished, and this process stably operated for 300 hours. The results are summarized as follows: 720 kg of 3,5-dimethylaniline, 142 kg of hydrofluoric acid and 2376 kg of 35% nitrosylsulfuric acid solution are totally consumed; 717.8 kg of 3,5-dimethyl fluorobenzene finished product is obtained, with a yield of 97.3% and a purity of 99.90%.

Example 6

The operation process in this example is the same as that in example 1, and the difference is the feeding ratio of aniline to hydrogen fluoride. The influence of different feeding ratios of aniline to hydrogen fluoride on reaction is researched. The results are summarized in Table 2.

TABLE 2

Influence of different feeding ratios of aniline to hydrogen fluoride on reaction

| Number | Molar ratio | Flow rate of aniline | Flow rate of hydrogen fluoride | Yield of fluorobenzene | Purity of fluorobenzene |
| --- | --- | --- | --- | --- | --- |
| 1 | 1:5  | 50 g/min | 53.7 g/min  | 90.3% | 99.80% |
| 2 | 1:8  | 50 g/min | 85.9 g/min  | 97.1% | 99.91% |
| 3 | 1:10 | 50 g/min | 107.4 g/min | 98.3% | 99.94% |
| 4 | 1:12 | 50 g/min | 128.9 g/min | 98.6% | 99.95% |
| 5 | 1:14 | 50 g/min | 150.3 g/min | 98.7% | 99.96% |
| 6 | 1:16 | 50 g/min | 171.8 g/min | 98.8% | 99.97% |
| 7 | 1:18 | 50 g/min | 193.3 g/min | 98.9% | 99.97% |
| 8 | 1:20 | 50 g/min | 214.8 g/min | 98.9% | 99.97% |
| 9 | 1:25 | 50 g/min | 268.4 g/min | 98.8% | 99.97% |

TABLE 2-continued

Influence of different feeding ratios of aniline to hydrogen fluoride on reaction

| Number | Molar ratio | Flow rate of aniline | Flow rate of hydrogen fluoride | Yield of fluorobenzene | Purity of fluorobenzene |
|---|---|---|---|---|---|
| 10 | 1:30 | 50 g/min | 322.1 g/min | 98.5% | 99.96% |
| 11 | 1:35 | 50 g/min | 375.8 g/min | 98.3% | 99.96% |
| 12 | 1:40 | 50 g/min | 429.5 g/min | 98.0% | 99.95% |
| 13 | 1:50 | 50 g/min | 536.9 g/min | 97.2% | 99.96% |

It can be seen from Table 2 that when the molar ratio of aniline to hydrogen fluoride is 1:(5~50), the reaction can be carried out well. Fluorobenzene has a yield of more than 90% and a purity of more than 99.80%. When the molar ratio of aniline to hydrogen fluoride is less than 1:8, the reaction yield decreases obviously. The reason is that hydrogen fluoride is used as not only a reaction raw material but also a reaction solvent in the reaction process. Too little amount of hydrogen fluoride is not conducive to the dissolution and dilution of the aniline hydrogen fluoride salt, resulting in poor movement of the reaction solution in the micro-channel reactor, the weak heat and mass transfer capacity and increased side reactions, so as to affect the reaction yield. Although excessive hydrogen fluoride does not have heat and mass transfer problems, it will increase the entrainment loss of products in hydrogen fluoride and reduce the reaction yield. Excessive hydrogen fluoride will also reduce the efficiency of synthesis and increase the recycle pressure of hydrogen fluoride.

Example 7

The operation process in this example is the same as that in example 1, and the difference is the feeding ratio of aniline to nitrosylsulfuric acid. The influence of different feeding ratios of aniline to nitrosylsulfuric acid on reaction is researched. The results are summarized in Table 3.

TABLE 3

Influence of different feeding ratios of aniline to nitrosylsulfuric acid on reaction

| Number | Molar ratio | Flow rate of aniline | Flow rate of 40% nitrosylsulfuric acid solution | Yield of fluorobenzene | Purity of fluorobenzene |
|---|---|---|---|---|---|
| 1 | 1:1.0 | 50 g/min | 170.6 g/min | 95.1% | 99.91% |
| 2 | 1:1.02 | 50 g/min | 174.0 g/min | 98.1% | 99.92% |
| 3 | 1:1.04 | 50 g/min | 177.4 g/min | 98.8% | 99.96% |
| 4 | 1:1.06 | 50 g/min | 180.8 g/min | 98.9% | 99.97% |
| 5 | 1:1.08 | 50 g/min | 184.2 g/min | 98.9% | 99.97% |
| 6 | 1:1.10 | 50 g/min | 187.6 g/min | 98.3% | 99.95% |
| 7 | 1:1.12 | 50 g/min | 191.0 g/min | 97.1% | 99.93% |
| 8 | 1:1.14 | 50 g/min | 194.4 g/min | 95.9% | 99.92% |
| 9 | 1:1.16 | 50 g/min | 197.9 g/min | 94.8% | 99.90% |
| 10 | 1:1.18 | 50 g/min | 201.3 g/min | 93.9% | 99.88% |
| 11 | 1:1.20 | 50 g/min | 204.7 g/min | 92.4% | 99.82% |

It can be seen from Table 3 that when the feeding ratio of aniline to nitrosylsulfuric acid is 1:(1.0~1.2), the reaction can be carried out well. Fluorobenzene has a yield of more than 90% and a purity of more than 99.80%. With the increase of the feeding ratio of nitrosylsulfuric acid, the yield of fluorobenzene increases and then decreases. The reason is that the theoretical amount of nitrosylsulfuric acid is 1 equivalent of the amount of aniline. In the actual reaction, nitrosylsulfuric acid is lost to a certain degree. When the amount of nitrosylsulfuric acid is insufficient, the yield of fluorobenzene increases with the increase of the amount of nitrosylsulfuric acid. However, when the amount of nitrosylsulfuric acid exceeds the actual demand, excessive nitrosylsulfuric acid existing in the system will trigger side reactions so as to decrease the yield of fluorobenzene.

Example 8

This example is the same as example 1, and the difference is the of diazotization reaction temperature. Influence of different diazotization temperatures on reaction is researched. The results are summarized in Table 4.

TABLE 4

Influence of diazotization temperatures on reaction

| Number | Diazotization temperature | Yield of fluorobenzene | Purity of fluorobenzene |
|---|---|---|---|
| 1 | −25° C. | 88.8% | 99.61% |
| 2 | −20° C. | 91.5% | 99.85% |
| 3 | −15° C. | 94.5% | 99.91% |
| 4 | −10° C. | 96.5% | 99.93% |
| 5 | −5° C. | 98.4% | 99.95% |
| 6 | 0° C. | 98.8% | 99.96% |
| 7 | 5° C. | 98.9% | 99.97% |
| 8 | 10° C. | 98.2% | 99.97% |
| 9 | 15° C. | 95.1% | 99.93% |
| 10 | 20° C. | 92.0% | 99.88% |
| 11 | 25° C. | 86.1% | 99.65% |

It can be seen from Table 4 that when the temperature of the diazotization reaction is −20~20° C., the reaction can be carried out well. Fluorobenzene has a yield of more than 90% and a purity of more than 99.80%. With the increase of temperature of the diazotization reaction, the yield and purity of fluorobenzene increase and then decrease. The reason is that when the temperature of the reaction is too low, the speed of the diazotization reaction is slow. When the holdup volume of the micro-channel reactor and the flow rate of the materials are fixed, the diazotization reaction cannot be carried out completely, resulting in the decrease of the reaction yield. When the temperature of the diazotization reaction is too high, a series of side reactions are easily triggered, such as hydrolysis and polymerization, resulting in the decrease of the reaction yield.

Example 9

This example is the same as example 1, and the difference is that the thermal decomposition reaction temperature is different. Influence of different thermal decomposition reaction temperatures on reaction. The results are summarized in Table 5.

increase of thermal decomposition reaction temperature, the yield and purity of fluorobenzene first increased and then decreased. The reason is that when the reaction temperature is too low, the thermal decomposition reaction speed is slow. When the holdup volume of the micro-channel reactor and the flow rate of the material are fixed, the thermal decomposition reaction cannot be carried out completely, resulting in the decrease of the reaction yield. When the thermal decomposition reaction temperature is too high, a series of side reactions are easily triggered, such as hydrolysis and polymerization, resulting in the decrease of the reaction yield.

Example 10

This example is the same as example 1, and the difference is that the feeding rate is changed on the premise of keeping the feeding ratios of aniline to hydrogen fluoride to nitrosylsulfuric acid fixed. Influence of different feeding rates on reaction is researched. The results are summarized in Table 6.

TABLE 6

Influence of feeding rates on reaction

| Number | Flow rate of fluorobenzene | Flow rate of hydrogen fluoride | Flow rate of 40% nitrosylsulfuric acid solution | Yield of fluorobenzene | Purity of fluorobenzene |
| --- | --- | --- | --- | --- | --- |
| 1 | 10 g/min | 43.0 g/min | 36.2 g/min | 84.8% | 99.68% |
| 2 | 20 g/min | 85.9 g/min | 72.3 g/min | 93.4% | 99.88% |
| 3 | 30 g/min | 128.9 g/min | 108.5 g/min | 96.5% | 99.93% |
| 4 | 40 g/min | 171.8 g/min | 144.6 g/min | 98.3% | 99.96% |
| 5 | 50 g/min | 214.8 g/min | 180.8 g/min | 98.9% | 99.97% |
| 6 | 60 g/min | 257.7 g/min | 217.0 g/min | 98.7% | 99.97% |
| 7 | 70 g/min | 300.7 g/min | 253.1 g/min | 98.1% | 99.96% |
| 8 | 80 g/min | 343.6 g/min | 289.3 g/min | 96.5% | 99.93% |
| 9 | 90 g/min | 386.6 g/min | 325.4 g/min | 94.1% | 99.90% |
| 10 | 100 g/min | 429.5 g/min | 361.6 g/min | 90.9% | 99.79% |
| 11 | 110 g/min | 472.5 g/min | 397.8 g/min | 87.1% | 99.65% |

TABLE 5

Influence of thermal decomposition temperatures on reaction

| Number | Thermal decomposition temperature | Yield of fluorobenzene | Purity of fluorobenzene |
| --- | --- | --- | --- |
| 1 | 30° C. | 85.8% | 99.72% |
| 2 | 40° C. | 91.5% | 99.91% |
| 3 | 50° C. | 95.5% | 99.93% |
| 4 | 60° C. | 97.8% | 99.96% |
| 5 | 70° C. | 98.9% | 99.97% |
| 6 | 80° C. | 97.5% | 99.95% |
| 7 | 90° C. | 94.9% | 99.93% |
| 8 | 100° C. | 91.1% | 99.83% |
| 9 | 110° C. | 82.6% | 99.61% |

It can be seem from Table 5 that when the temperature of thermal decomposition reaction is 40~100° C., the reaction can be carried out well. The yield of fluorobenzene is more than 90% and the purity is more than 99.8%. With the For a fixed full continuous flow reaction device, since its size has been defined, especially the micro-channel reactors C, E and F as the main reaction equipment, their internal structures and holdups have been fixed. Therefore, when the flow rate of the material changes, the movement state and residence time of the material in the micro-channel reactor will inevitably change. As an important parameter for the operation of the full continuous flow reactor, the flow rate of the material together with the micro-channel reactor structure, operation temperature, material ratios and the like forms a group of interrelated complex parameters, which determines the success or failure of the full continuous flow synthesis process. When the micro-channel reactor structure, operation temperature and material ratios are fixed, an optimal flow rate is necessarily present to be matched with the above fixed parameters. The optimal flow rate can only be obtained after a long period of equipment operation and debugging. At the optimal flow rate, it is ensured that the material is in the most appropriate residence time and the best movement state in the reactor, so that the reaction can be carried out under the optimal state, thereby obtaining the optimal reaction results.

We claim:
1. A full continuous flow synthesis process of fluorine-containing aromatic hydrocarbon compounds, comprising the following steps:
   (1) according to a feeding ratio of aromatic amine to hydrogen fluoride, pumping aromatic amine into a thermostat A, pumping hydrogen fluoride into thermostat B, and keeping the temperatures of materials constant;
   (2) allowing aromatic amine and hydrogen fluoride flowing out from the thermostats to flow into a micro-channel reactor C for a salt forming reaction to obtain a hydrofluoric acid solution of an aromatic amine hydrogen fluoride salt;
   (3) pumping a sulfuric acid solution of nitrosylsulfuric acid into a thermostat D according to a feeding ratio of nitrosylsulfuric acid to aromatic amine, and keeping the temperatures of materials constant;
   (4) allowing the hydrofluoric acid solution of the aromatic amine hydrogen fluoride salt flowing out from the micro-channel reactor C and the sulfuric acid solution of nitrosylsulfuric acid flowing out from the thermostat D to flow into a micro-channel reactor E for diazotization reaction to obtain an aryl diazonium salt solution;
   (5) allowing the aryl diazonium salt solution flowing out from the micro-channel reactor E to flow into a micro-channel reactor F for a thermal decomposition reaction to obtain a mixture consisting of fluorine-containing aromatic hydrocarbons, hydrofluoric acid, sulfuric acid and nitrogen;
   (6) allowing the mixture consisting of fluorine-containing aromatic hydrocarbons, hydrofluoric acid, sulfuric acid and nitrogen to flow through a cooler G and then enter a three-phase separator H for continuous separation, discharging nitrogen at a gas outlet of the three-phase separator H, allowing a fluorine-containing aromatic hydrocarbon crude product to flow out from a light liquid phase outlet of the three-phase separator H, and allowing a mixture of hydrofluoric acid and sulfuric acid to flow out from a heavy liquid phase outlet of the three-phase separator H;
   (7) spraying nitrogen discharged from the gas outlet of the three-phase separator H in a spray tower I to remove acid, and then discharging;
   (8) allowing the fluorine-containing aromatic hydrocarbon crude product flowing out from the light liquid phase outlet of the three-phase separator H to enter a continuous alkaline washing tower J for alkaline washing to remove acid, followed by dehydrating in a continuous drying tower K and rectifying in a continuous rectification tower L, so as to obtain a fluorine-containing aromatic hydrocarbon finished product; and
   (9) distilling the mixture of hydrofluoric acid and sulfuric acid flowing out from the heavy liquid phase outlet of the three-phase separator H in a continuous distillation tower M to obtain recycled hydrogen fluoride and recycled sulfuric acid.

2. The full continuous flow synthesis process of fluorine-containing aromatic hydrocarbon compounds according to claim 1, wherein in step (1), the aromatic amine is selected from any one of: aniline, o-methylaniline, m-methylaniline, p-methylaniline, o-ethylaniline, m-ethylaniline, p-ethylaniline, 2,3-dimethylaniline, 2,4-dimethylaniline, 2,5-dimethylaniline, 2,6-dimethyl aniline, 3,4-dimethyl aniline, 3,5-dimethylaniline, 2,3,4-trimethylaniline, 2,3,5-trimethylaniline, 2,3,6-trimethylaniline, 2,4,5-trimethylaniline, 2,4,6-trimethylaniline, 3,4,5-trimethyl aniline, 2,3,4,5-tetramethylaniline, 2,3,5,6-tetramethylaniline, 2,3,4,6-tetramethylaniline and pentamethylaniline.

3. The full continuous flow synthesis process of fluorine-containing aromatic hydrocarbon compounds according to claim 1, wherein in step (1), the water content of hydrogen fluoride is less than 1.0%.

4. The full continuous flow synthesis process of fluorine-containing aromatic hydrocarbon compounds according to claim 1, wherein in step (1), a molar ratio of aromatic amine to hydrogen fluoride is 1:5~50.

5. The full continuous flow synthesis process of fluorine-containing aromatic hydrocarbon compounds according to claim 1, wherein in step (1), the temperature of aromatic amine whose temperature is kept constant in the thermostat A is −20~70° C., and a temperature fluctuation is less than ±2° C.

6. The full continuous flow synthesis process of fluorine-containing aromatic hydrocarbon compounds according to claim 1, wherein in step (1), the temperature of hydrogen fluoride whose temperature is kept constant in the thermostat B is −50~20° C., and a temperature fluctuation is less than ±2° C.

7. The full continuous flow synthesis process of fluorine-containing aromatic hydrocarbon compounds according to claim 1, wherein in step (2), the temperature of the material at the outlet of the micro-channel reactor C is controlled to −10~20° C., and a temperature fluctuation is less than ±2° C.

8. The full continuous flow synthesis process of fluorine-containing aromatic hydrocarbon compounds according to claim 1, wherein in step (3), the effective content of nitrosylsulfuric acid in the sulfuric acid solution of nitrosylsulfuric acid is 10%~50%.

9. The full continuous flow synthesis process of fluorine-containing aromatic hydrocarbon compounds according to claim 1, wherein in step (3), the temperature of sulfuric acid solution of nitrosylsulfuric acid whose temperature is kept constant in the thermostat D is −30~50° C., and a temperature fluctuation is less than ±2° C.

10. The full continuous flow synthesis process of fluorine-containing aromatic hydrocarbon compounds according to claim 1, wherein in step (3), a molar ratio of aromatic amine to nitrosylsulfuric acid is 1:1~1.2.

11. The full continuous flow synthesis process of fluorine-containing aromatic hydrocarbon compounds according to claim 1, wherein in step (4), the temperature of the material in the micro-channel reactor E is controlled to −20~20° C., the temperature of the material at the outlet is controlled to −20~20° C., and a temperature fluctuation is less than ±2° C.

12. The full continuous flow synthesis process of fluorine-containing aromatic hydrocarbon compounds according to claim 1, wherein in step (5), the temperature of the material in the micro-channel reactor F is controlled to 20~100° C., the temperature of the material at the outlet is controlled to 20~100° C., and a temperature fluctuation is less than ±2° C.

13. The full continuous flow synthesis process of fluorine-containing aromatic hydrocarbon compounds according to claim 1, wherein in step (6), the temperature of the material at the outlet of the cooler G is controlled to −20~20° C.

14. The full continuous flow synthesis process of fluorine-containing aromatic hydrocarbon compounds according to claim 1, wherein in step (6), the temperature of the material at the outlet of the three-phase separator H is controlled to −20~20° C.

15. The full continuous flow synthesis process of fluorine-containing aromatic hydrocarbon compounds according to claim 1, wherein in step (7), the spraying method of the spray tower I is selected from any one of: single-stage alkaline solution spray, multi-stage alkaline solution spray and comprehensive water and alkaline solution spray.

16. The full continuous flow synthesis process of fluorine-containing aromatic hydrocarbon compounds according to claim 1, wherein in step (7), the spray tower I is structurally selected from any one of: a packed tower and a plate tower.

17. The full continuous flow synthesis process of fluorine-containing aromatic hydrocarbon compounds according to claim 15, wherein in step (7), an alkaline solution for spraying in the spray tower I is an aqueous solution of an inorganic alkali, the inorganic alkali is selected from one or more of: sodium hydroxide, potassium hydroxide, sodium carbonate and potassium carbonate, and the pH value of the alkaline solution is more than 9.

18. The full continuous flow synthesis process of fluorine-containing aromatic hydrocarbon compounds according to claim 15, wherein in step (7), the operation temperature of the spray tower I is a normal temperature.

19. The full continuous flow synthesis process of fluorine-containing aromatic hydrocarbon compounds according to claim 1, wherein in step (8), the continuous alkaline washing tower J adopts liquid-phase countercurrent, the alkaline solution enters from the upper part of the continuous alkaline washing tower J and then flows out from the bottom of the continuous alkaline washing tower J after undergoing two-phase separation, the fluorine-containing aromatic hydrocarbon crude product enters from the lower part of the continuous alkaline washing tower J and then flows out from the top of the continuous alkaline washing tower J after undergoing two-phase separation.

20. The full continuous flow synthesis process of fluorine-containing aromatic hydrocarbon compounds according to claim 19, wherein in step (8), the alkaline solution used in the continuous alkaline washing tower J is an aqueous solution of inorganic alkali, the inorganic alkali is selected from one or more of: sodium hydroxide, potassium hydroxide, sodium carbonate and potassium carbonate, and the pH value of the alkaline solution is more than 9.

21. The full continuous flow synthesis process of fluorine-containing aromatic hydrocarbon compounds according to claim 1, wherein in step (8), the operation temperature of the continuous alkaline washing tower J is a normal temperature.

22. The full continuous flow synthesis process of fluorine-containing aromatic hydrocarbon compounds according to claim 1, wherein in step (8), the continuous rectifying tower L is structurally selected from any one of: a packed tower and a plate tower.

23. The full continuous flow synthesis process of fluorine-containing aromatic hydrocarbon compounds according to claim 1, wherein in step (9), the continuous distillation tower M is structurally selected from any one of: a packed tower and a plate tower.

* * * * *